United States Patent [19]

Markham

[11] Patent Number: 4,822,816

[45] Date of Patent: Apr. 18, 1989

[54] COMPOSITIONS AND METHODS FOR ADMINISTERING VITAMIN C

[75] Inventor: Richard G. Markham, Prescott, Ariz.

[73] Assignee: Oxycal Laboratories, Inc., Prescott, Ariz.

[21] Appl. No.: 36,598

[22] Filed: Apr. 10, 1987

[51] Int. Cl.[4] .................... A01N 43/08; A61K 31/335
[52] U.S. Cl. .................................................... 514/474
[58] Field of Search ............... 514/474, 922, 163, 460, 514/473; 424/10

[56] References Cited

U.S. PATENT DOCUMENTS 3,459,863  8/1969  Apelian et al. ....................... 514/474
3,781,423  12/1973  Aoka et al. ........................... 514/474

OTHER PUBLICATIONS

Lewin–Vitamin C its Molecular Biology and Medical Potential, Academic Press (1976).

Primary Examiner—Douglas W. Robinson
Assistant Examiner—Roger E. Gobrogge
Attorney, Agent, or Firm—William H. Drummond

[57] ABSTRACT

A composition useful for administering Vitamin C to a subject comprises a compound having Vitamin C activity and at least one compound selected from the class consisting of the aldono-lactones and edible salts of L-threonic, L-xylonic and L-lyxonic acids.

High Vitamin C levels in the human body are established by orally administering to a human subject an effective amount of this composition.

2 Claims, No Drawings

COMPOSITIONS AND METHODS FOR ADMINISTERING VITAMIN C

This invention relates to an improved form of Vitamin C.

In another respect, the invention concerns improved methods for establishing Vitamin C levels in the human body.

In yet another respect, the invention pertains to methods for improving the human body tolerance to Vitamin C.

In still another respect, the invention relates to a Vitamin C derivative composition which is more effectively absorbed and retained in the human body.

Prior workers have identified over 300 separate metabolic mechanisms in which Vitamin C is involved in physiologic reactions. These mechanisms range from the antiscorbutic effect first observed by Dr. Robert Lind in 1740 to more recently discovered anti-oxidant free-radical scavenging reactions, the co-reaction with enzymes in the formation of collagen, energy metabolism accentuation in the polynuclearleucosites and facilitation of iron absorption.

The clinical effects of such metalbolic reactions have been widely recognized and reported. For example, the free-radical scavenging effect is believed to enable the body to convert carcinogens to non-toxic derivations which are eliminated in the urine and, consequently, to ameliorate the effects of smoking and exposure of the body to other environmental pollutants. Animal studies have demonstrated that body enzymes convert ascorbates to oxidation products which have demonstrated tumor growth inhibition.

Consequently, there is little scientific doubt that the establishment and maintenance of effective levels of Vitamin C and its derivatives in the human body yield important health advantages. The presence of Vitamin C in substantial concentration has been observed in the adrenals, ovaries, brain, pituitaries, liver, spleen, blood cells, blood serum, and extracellular lung liquids.

Most animals have a liver enzyme which enables them to actually mantufacture Vitamin C in situ by conversion of blood sugar into ascorbic acid. However, humans do not have this enzymes. As a consequence, the Vitamin C which is required by the human body for the various metabolic reactions discussed above must be ingested with the human diet. Futhermore, the human body does not have the ability to store Vitamin C—if unmetabolized, it is excreted. Low levels of Vitamin C and its derivations in the human body produce a variety of undesirable physiological responses and extremely low levels produce extreme responses which may result in death, e.g., from scruvy. Wholly apart from these "normal" requirements of Vitamin C, it is important in some therapeutic modalities to establish and maintain above-normal Vitamin C levels in the body. These above-normal concentrations are difficult to establish and maintain because the human body exhibits on a finite tolerance for Vitamin C, with resultant diarrhea and other side reactions, such as gastric irritation and inflammation if these tolerances are exceeded.

I have now discovered compositions and methods for improving the establishment and maintenance of high levels of Vitamin C (including its derivatives) in the human body. Briefly, the composition which I have discovered comprises a compound having Vitamin C activity and at least one compound selected from the class consisting of the aldono-lactones and edible salts of L-threonic, L-xylonic and L- lyxonic acids.

A method which I have discovered for establishing Vitamin C levels in the human body includes the step of orally administering this composition to a subject.

Another method of the invention comprises the step of converting L-ascorbic acid to this composition and orally administering this composition to the subject.

As used herein, the term "compound having Vitamin C activity" means Vitamin C (L-ascorbic acid) and any derivative thereof which exhibits ascorbitic activity as determined by the standard iodine titration test. Such derivatives include, for example, oxidation products such as dehydroascorbic acid and edible salts of ascorbic acid such as, illustratively, calcium, sodium, magnesium, potassium and zinc ascorbates.

The metabolites of ascorbic acid and its derivatives include the aldo-lactones and edible salts of aldonic acids. As will appear, the compositions of the present invention are characterized by the presence of at least one or more of these metabolites corresponding to three specific aldonic acids: L-threonic acid, L-xylonic acid and L-lyxonic acid.

The presence of one or more of these metabolites in the compositions of the invention is both a convenient way of identifying such compositions and is also necessary to achieve the desired result, improvement in Vitamin C absorption and/or retention.

The component of the compositions of the invention which, as indicated above, has "Vitamin C activity" can be L-ascorbic acid or any of its derivatives which have the ability to provide the ascorbic/ascorbate moiety in physiologic processes, e.g., dehydroascorbic acid, calcium ascorbate which are most commonly employed in Vitamin C food supplements, as well as a wide variety of other edible (nontoxic) salts such as potassium, sodium, magnesium and zinc ascorbate. In general, any such compound which exhibits C-vitaminic activity will suffice and this can be conveniently determined by the well-known standard "iodine test".

A suitable method for preparing the compositions of the invention comprises reacting L-ascorbic acid with a non-toxic metal compound, e.g., calcium carbonate, sodium bicarbonate, under oxidizing conditions at an elevated temperature, e.g., 40° C.-98° C., to convert a substantial proportion of the ascorbic acid to its corresponding salt, e.g., calcium or sodium ascorbate, and drying the reaction mixture to produce a solid produce of essentially neutral pH (e.g., 6.0-7.2). Preferably, a slight stoichiometric excess of the metal salt reactant is provided. The resultant product has an iodine ascorbate activity in the range 100-400 mg./500 mg. sample with the higher activity preferred for practical reasons. Longer heating at oxidizing conditions produces lower iodine ascorbate activity.

The compositions of the invention appear useful in administering Vitamin C to patients who have low ascorbic acid tolerance. In particular, paatients who have a tendency to form kidney stones are particularly susceptible to difficulties when ingesting ascorbic acid and its common derivatives, calcium ascorbate, which cause elevated urine oxalate levels. It has now, however, been discovered that the compositions of the present invention can be administered without increasing the oxalate level in the urine to the levels encountered when the prior art compositions are ingested. Therefore, the present compositions and methods are especially suitable as a means of establishing and maintaining ascorbate body levels in such kidney stone-prone subjects.

The following examples are presented for purposes of illustrating the practice of the invention and are not intended as limitations on the scope thereof.

EXAMPLE 1

To an 80 gallon, steam-heated stainless steel reaction vessel was added 60 lbs. of hot (44° C.) water.

Ascorbic acid-U.S.P., 110.23 lbs., was added in one portion to the hot water. The resulting slurry was mechanically stirred and heated with steam (pressure 15 p.s.i.) until a temperature of 70° C. was achieved.

To the aqueous slurry of ascorbic acid was added 23 lbs. of calcium carbonate. The incremental addition of the carbonate required 3-4 minutes. The reaction mixture appeared gray in color and much foaming due to the evolution of $CO_2$ was evident.

After eight minutes of stirring, most of the foaming had subsided and the reaction mixture appeared red-brown in color. The reaction temperature was 80° C.

Stirring and heating were continued for 15 minutes until the temperature of the reaction mixture reached 98° C. where it was maintained for an additional 20 minutes, during which an additional 8.25 lbs. of calcium carbonate was added, with stirring. The reaction mixture was then pumped to a double-drum steam-heated dryer (surface temperature 250° F.). The pump-drying step required 35 minutes. The dried product was light-tan color and the yield was approximately 120 pounds of product.

Assays were performed immediately on 5.00 g. samples dissolved in 500 ml. distilled water.

The material collected during the drying process showed 400 mg. ascorbate activity per 500 mg. by the standard iodine titration technique. The same aqueous solution showed pH 7.0.

EXAMPLE 2

The following example describes clinical tests comparing the product of Example 1 (test) with L-ascorbic acid and citric acid (placebo), measuring intracellular ascorbate levels, urinary ascorbate output and urinary oxalate excretion at various times after ingestion of standard doses of the test, L-ascorbic acid and placebo.

Summary of the Protocol

Twelve men, agaes 27 to 45, were studied.

All were instructed that they should be on a low Vitamin C diet for one week prior to the study. (No citrus products and no large amounts of green leafy vegetables).

Following overnight fast, blood and 24-hour urine samples were take. White blood cell and 24-hour urinary ascorbate and oxalate levels were determined and correlated with serum ascorbate levels.

The 12 men were divided into three groups, and were given the following supplements:
(a) Test Group: 4000 MG* per day of the product Ex. 1. *4000 MG is equivalent in ascorbate activity (iodine test) to 3000 MG L-ascorbic acid.
(b) Ascorbate Group: 3000 MG of L-ascorbic per day.
(c) Citric Acid Group: 3000 MG of citric acid per day.

All 12 continued on the low Vitamin C diet. Blood samples were taken at 0, 4, 8 and 24 hours after morning ingestion of the designated supplements. Urinary 24-hour ascorbate and oxalate levels were determined.

After a wash-out period (varying from two days to several days, due to job situation of the participants), the groups were switched to another supplement, as follows:
(a) Test group to citrate group.
(b) Citrate group to ascorbate group.
(c) Ascorbate group to test group.

Supplements were taken at the same level (4000 MG of EX. 1 product, 3000 MB of L-ascorbic and 3000 MG of citric acid) by all three groups. Blood samples were again drawn at 0, 4, 8 and 24 hours from time of ingestion. A 24-hour urine was also collected by all 12 participants at the end of the period. Again, all specimens were analyzed for their respective concentration of ascorbate and oxalate level.

Analytical Procedures

The analytical procedures utilized are described in:

*Clinical Chemistry, Principles and Techniques*, edited by Richard J. Henry, Donald D. Cannon and James W. Windelman, Harper and Row, 1974, p. 1393-1398.

*Standard Methods of Clinical Chemistry*, J. S. Roe, edited by Seligson D. New York, Academic Press, 1961, Vol. 3, p. 35.

In the quantitation of 24-hour urine oxalate, an aliquot of urine is shaken with an adsorbent which selectively binds the oxalate. The extracted urine is discarded and the oxalate is eluted from the adsorbent with dilute alkali.

Oxalate is oxidized to hydrogen peroxide and carbon dioxide by oxalate oxidase. The hydrogen peroxide reacts with 3-methyl-2-benzothiozolinone hydrazone (MBTH) and 3(dimenthylamino)benzoic acid (DMAB) in the presence of peroxidase to yield an indamine dye with a maximum absorbance at 590 NM.

The urine oxalate text is further described in the following references:

Hodgekinson, A.: *Oxalic Acid in Viology and Medicine*, Academic Press, New York, 1977.

Robertson, W. D.; Rutherford, A.: *Aspects of the Analysis of Oxalate in Urine*, Scan J. Uro Nephrol, Suppl. 53, pg. 85, 1979.

Lamden, M. P.; Chrystowski, G. A.: *Urinary Oxalate Excretion by Main Following Ascorbine Acid Ingestion*, Prog. Soc. Exp. Biol. Med. 85:190, 1954.

Costello, J.: *The Effect of Ascorbic Acid on Oxalate Metabolism in Human Biochemistry and Clinical Pathology*, edited by G. A. Rose, W. G. Robertson and R. W. E. Watts. Proceedings of an International Meeting in London, 1971, pp. 270-273.

The results of this clinical study are set forth below:

TABLE 1

|  | Percent Change* in Group | | |
| --- | --- | --- | --- |
|  | Citrate | L-ascorbic | Test |
| Serum Ascorbate Level | | | |
| 4th Hour | 10 | 180.3 | 264.8 |
| 8th Hour | 19.6 | 91.6 | 144.2 |
| 24th Hour | 5.9 | 24.6 | 56.2 |
| 7th Day |  | 45.3 | 102.5 |
| White Blood Cell (WBC) Ascorbate Level | | | |
| 4th Hour | −40.5 | 34.1 | 38 |
| 8th Hour | −21.2 | −21.9 | −6.80 |
| 24th Hour | −6.3 | −5.3 | 18.2 |
| 7th Day |  | 27.6 | 30.5 |

TABLE 1-continued

|  | Percent Change* in Group | | |
| --- | --- | --- | --- |
|  | Citrate | L-ascorbic | Test |
| 24th Hour Urine Ascorbate | | | |
| % Change | 27.7 | 2760.6 | 486.3 |
| MG/24 Hour | 43.65 | 314.5 | 252 |
| 7th Day Urine Ascorbate | | | |
| % Change |  | 4583 | 617 |
| MG/24 Hour |  | 459 | 321 |
| 24th Hour Urine Oxalate | | | |
| % Change | 7 | 162 | 35.9 |
| MG/24 Hr. | 25.9 | 63.8 | 41.6 |

*increase unless otherwise indicated.

The conclusions which were drawn from this study are:

Serum Ascorbate Level:
At 4, 8 and 24 hours and 7 days later, test groups had higher serum ascorbate level as compared to both the citrate group and the L-ascorbic group.

WBC Ascorbate Level:
Although all 8th hour WBC ascorbate groups showed an average decrease, test group had the smallest percentage decrease. Four and 24-hour measurement plus the 7th day level showed that test group was able to maintain the highest white blood cell ascorbate level.

24-Hour WBC Ascorbate:
24-hour post various loadings of: citrate, L-ascorbic and test produce --
Both the citrate group and L-ascorbic group showed a decrease in WBC ascorbate levels. Test group maintained a much higher level compared to baseline.

7 Days Post Loading of L-Ascorbic and Test:
Average percentage change in WBC Ascorbate is still higher in the Test Group than in the L-ascorbic group.

24-Hour Urine Ascorbate Output:
Both in average percentage change and in absolute total means values, the test groups had less ascorbate output than L-ascorbic.

7 Days - 24 Hour Urinary Ascorbate Output:
Test groups have less ascorbate output than the citrate and the L-ascorbic groups.

24-Hour Urinary Oxalate Output:
Oxalate output is greatly decreased in the test group as compared to the ascorbic group. This means that while taking test produce as a supplement, a person has less chance of forming oxalate-containing kidney calculi than a person taking L-ascorbic.

7 Day 24 Hour Oxalate Output:
Prolonged supplementation with test product leads to less excretion of urinary oxalate than supplementation with L-ascorbic.

EXAMPLE 3

To a 2-liter, reaction vessel equipped with an agitator and a thermometer is added 300 ml distilled water and 440 g (2.5 moles) L-ascorbic acid. To this stirred slurry, finely divided calcium carbonate is added incrementally at a rate such as to produce a constant evolution of carbon dioxide (reaction byproduct), the reaction temperature being maintained at about 20° C. The addition of calcium carbonate is suspended after about 25 g to 37.5 g have been added (representing from about 20% to 30% of that required for complete reaction with the L-ascorbic acid charge).

At this point, the temperature is raised to 80° C. Further additions of calcium carbonate are begun, the temperature being maintained in the range 60° C. to about 70° C. The total quantity of calcium carbonate added is 125 g (1.25 moles).

The reaction mixture is transferred to a shallow container maintained at a temperature of between 60° C. and 80° C., for a period of from 12 to 36 hours, during which time the pH of the mixture rises to a pH range of 6.0-7.0. At this point, the excess water is removed under vacuum.

The dry products are light tan in color and readily soluble in water, except for unreacted calcium carbonate, to produce neutral solutions.

EXAMPLE 4

Clinical studies using the product of Example 3 yield similar results to those set forth in Example 2.

EXAMPLE 5

The products of Examples 1 and 3 are subjected to qualitative analysis, as follows:

Ascorbic acid, calcium ascorbate and dehydroascorbic acid were separated from the product by chromatography and the residue was subjected to nuclear magnetic resonance spectroscopy. Likely possibilities for the structures of the components detected by spectroscopy were formulated and these authentic compounds were then synthesized. After nmr spectra of these authentic compounds were obtained, they were compared to the nmr spectra of the test specimens. A match of the spectra was used to identify the components of the test specimens.

The techniques employed were $^1$H and $^{13}$C nmr. The aldonic acid salts identified are the calcium salts of L-threonic acid, L-xylonic acid and L-lyxonic acid.

EXAMPLE 6

The procedures of Example 1 are repeated except that the reactant added to the ascorbic acid is changed to yield correspondingly different edible salts of ascorbic acid.

| Reactant | Salt |
| --- | --- |
| sodium bicarbonate | sodium ascorbate |
| magnesium carbonate | magnexium ascorbate |
| potassium bicarbonate | potassium ascorbate |
| zinc oxide | zinc ascorbate |

These products produce similar physiological results to those described in Example 2 and contain the aldonic acid salts corresponding to those identified in Example 5.

EXAMPLE 7

Quantitative analysis of the products of Examples 1, 4 and 6 is performed. The products have the indicated compositions:

|  | Wt. % |
| --- | --- |
| Anhydrous metal Ascorbate | 80-82 |
| Unreacted metal reagent | 6-7 |
| Dehydroascorbic Acid | 3-8 |
| Moisture | 1.5—3 |
| Aldonic Acid Derivatives | 5-6 |

The aldonic acid derivatives include derivatives of the indicated acid in the following approximate proportions:

| Acid (Derivative) | Parts by Weight |
| --- | --- |
| Threonic | 8 |
| Xylonic | 3 |
| Lyxonic | 1 |

There are indications that one or more of these aldonic acids may be partially linked.

EXAMPLE 8

Animal feeding studies of the product of Example 1 provide similar results to the human studies of Example 2.

EXAMPLE 9

The procedure of Example 1 is repeated except that no metal compound reactant (e.g., calcium carbonate) is added. The ascorbic acid is, however, subjected to the same oxidizing, heating, drying steps. The product consists of anhydrous ascorbic acid product, DHA water and also-lactone derivatives of threonic, xylonic and lyxonic acids. This product yields similar physiological results to those described in Example 8.

EXAMPLE 10

The procedures of Example 2 are repeated except that the test product is synthesized by mixing reagent grade calcium ascorbate with Test A—Threonic Acid (calcium salt)
Test B—Xylonic Acid (calcium salt)
Test C—Lyxonic Acid (calcium salt)
in the same weight proportions as the components are found in Example 7.

The tests of Example 2 are repeated using these test compounds and using pure calcium ascorbate as an additional control.

These tests confirm that the physiological activity of the mixed ascorbate-aldonic product is due to the aldonic component and that any one of these aldonic components causes the similarly improved absorption and retention of the Vitamin C component.

Having described my invention in such terms as to enable those skilled in the art to understand and practice it, and having identified the presently preferred embodiments thereof, I claim:

1. A vitamin composition comprising:
   (a) an effective amount of a compound having Vitamin C activity, selected from the group consisting of (i) dehydroascorbic acid, (ii) L-ascorbic acid and the edible salts thereof; and
   (b) at least one compound selected from the group consisting of the aldono-lactones of L-threonic acid, L-xylonic acid, L-lyxonic acid and the edible salts of L-threonic acid, L-xylonic acid and L-lyxonic acids, in an amount effective to increase the human body absorption rate of said Vitamin C compound.

2. A method for establishing high Vitamin C levels in the human body which comprise the step of orally administering to a subject an effective amount of the composition of claim 1.

* * * * *

UNITED STATES PATENT AND TRADEMARK OFFICE
CERTIFICATE OF CORRECTION

PATENT NO.    :   4,822,816
DATED         :   April 18, 1989
INVENTOR(S)   :   Richard G. Markham It is certified that error appears in the above-identified patent and that said Letters Patent is hereby corrected as shown below:

Column 1, line 28, delete "derivations" and insert "derivatives"

Column 1, line 50, delete "derivations" and insert "derivatives"

Column 1, line 59, delete "on" and insert "only"

Column 2, line 49, delete "produce" and insert "product"

Column 3, line 28, delete "pump-drying" and insert "pumping-drying"

Column 3, line 55, delete "take" and insert "taken"

Column 4, line 11, delete "MB" and insert "MG"

Column 4, line 38, delete "text" and insert "test"

Column 5, line 46, delete "produce" and insert "product"

Column 7, line 22, delete "also-lactone" and insert "aldo-lactone"

Signed and Sealed this

Sixteenth Day of January, 1990

*Attest:*

JEFFREY M. SAMUELS

*Attesting Officer*       *Acting Commissioner of Patents and Trademarks*